United States Patent
Eifler et al.

(10) Patent No.: US 9,833,418 B2
(45) Date of Patent: Dec. 5, 2017

(54) TRANSDERMAL THERAPEUTIC SYSTEM HAVING CONTROLLED ACTIVE SUBSTANCE FLOW COMPRISING A BASIC REACTING OXIDE

(75) Inventors: René Eifler, Koblenz (DE); Regine Kaufmann, Neuwied (DE); Patrick Mohr, Bad Breisig (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 13/321,586

(22) PCT Filed: May 19, 2010

(86) PCT No.: PCT/EP2010/003078
§ 371 (c)(1),
(2), (4) Date: Nov. 21, 2011

(87) PCT Pub. No.: WO2010/136149
PCT Pub. Date: Dec. 2, 2010

(65) Prior Publication Data
US 2012/0065599 A1     Mar. 15, 2012

(30) Foreign Application Priority Data
May 27, 2009  (DE) .......................... 10 2009 022 915

(51) Int. Cl.
A61K 9/70      (2006.01)
A61K 47/02     (2006.01)
A61K 31/13     (2006.01)

(52) U.S. Cl.
CPC ............ *A61K 9/7061* (2013.01); *A61K 31/13* (2013.01); *A61K 47/02* (2013.01); *Y10T 156/10* (2015.01)

(58) Field of Classification Search
None
See application file for complete search history.

(56) References Cited

U.S. PATENT DOCUMENTS

| | | | |
|---|---|---|---|
| 6,565,879 B1 | 5/2003 | Luo et al. | |
| 7,175,853 B1 * | 2/2007 | Bracht | A61M 31/002 424/443 |
| 2001/0038862 A1 | 11/2001 | Luo et al. | |
| 2006/0078601 A1 * | 4/2006 | Kanios et al. | 424/449 |
| 2006/0093659 A1 | 5/2006 | Luo et al. | |
| 2008/0138388 A1 * | 6/2008 | Aida | A61K 9/7061 424/448 |
| 2012/0245537 A1 * | 9/2012 | Horstmann et al. | 604/290 |

FOREIGN PATENT DOCUMENTS

| | | | |
|---|---|---|---|
| WO | WO 01/43734 A2 | 6/2001 | |
| WO | WO 01/43775 A2 | 6/2001 | |

* cited by examiner

*Primary Examiner* — Ernst V Arnold
*Assistant Examiner* — Kyung Sook Chang
(74) *Attorney, Agent, or Firm* — ProPat, L.L.C.

(57) ABSTRACT

The present invention relates to transdermal therapeutic systems that include an occlusive back layer impervious to an active substance, a single or multilayer matrix, and a peelable protective film. The matrix or at least one of the matrix layers includes a pharmaceutical active substance or a plurality of pharmaceutical active substances in the form of at least one pharmaceutically consumable salt thereof and a pharmaceutically consumable, alkaline reacting oxide.

22 Claims, No Drawings

TRANSDERMAL THERAPEUTIC SYSTEM HAVING CONTROLLED ACTIVE SUBSTANCE FLOW COMPRISING A BASIC REACTING OXIDE

CROSS-REFERENCE TO RELATED APPLICATIONS

This application is being filed under Rule 1.371 as a National Stage Application of pending International Application No. PCT/EP2010/003078 filed May 19, 2010, which claims priority to the following parent application: German Patent Application No. 10 2009 022 915.9, filed May 27, 2009. Both International Application No. PCT/EP2010/003078 and German Patent Application No. 10 2009 022 915.9 are hereby incorporated by reference herein in their entirety.

FIELD OF THE INVENTION

The present invention relates to preparations for transdermal administration of pharmaceutical active ingredients, more particularly transdermal therapeutic systems (TTS).

BACKGROUND OF THE INVENTION

Transdermal therapeutic systems are administration forms which have a layered structure and comprise at least one active ingredient-containing polymer layer and one active ingredient-impermeable backing layer. Transdermal therapeutic systems are also referred to as active-ingredient patches. They permit long-lasting administration of the pharmaceutical active ingredient contained therein to the skin or via the skin of a patient to be treated.

For transdermal administration of active ingredients via the skin in a therapeutically necessary dose, the active ingredient to be administered must have sufficient skin permeability. Therefore, for the purposes of developing transdermal therapeutic systems, active ingredients in the form of their free base (active-ingredient base) are preferably used. Active-ingredient bases usually have good permeation properties for transdermal administration which are considerably better than those of the salts of the corresponding active ingredient. In addition, active-ingredient bases can be easily processed during preparation of active ingredient-containing masses for transdermal preparations. Also, owing to their rapid availability in transdermal therapeutic systems, active ingredients in the form of their free base are used preferentially over the salts of the corresponding active ingredient.

For the resulting transdermal preparations, there are further advantages: the weight of the matrix is lower and/or the active-ingredient concentration in the matrix can be lower, the concentration of permeation enhancer can be reduced or permeation enhancers can be completely omitted, and it is possible to produce transdermal therapeutic systems having other adhesive properties.

However, production of transdermal therapeutic systems having an active ingredient in the form of its free base, and transdermal therapeutic systems having an active ingredient in the form of its free base, can also have disadvantages. For instance, the active-ingredient base must be stored at low temperatures, i.e., at 4° C. or at lower temperatures, to avoid undesired degradation of the active ingredient. Storage at low temperatures is also advisable when the active-ingredient base is highly volatile, in order to prevent the pressure in the container storing the active-ingredient base from becoming too great.

Problems may also occur when preparing active ingredient-containing masses or when coating support materials with said active ingredient-containing masses. If use is made of an active-ingredient base having a high vapor pressure (e.g., identifiable by a low evaporation number), this may result in considerable losses of active ingredient during coating and subsequent drying of the preparation.

In addition, antioxidants often need to be used to stabilize the active-ingredient base, in order to prevent or to at least reduce interactions between the active-ingredient base and other constituents of the transdermal therapeutic system, for example the pressure-sensitive adhesive, the permeation enhancer, the excipients, the backing layer or the protective sheet.

Undesired interactions between an active-ingredient base and ambient air are also possible. For instance, the moisture in the air may lead to hydrolysis of the active-ingredient base. However, an undesired reaction between the active-ingredient base and the moisture in the air can only be avoided by a complicated production process in which the transdermal therapeutic systems are sealed in the packaging material pouch without intermediate storage and with introduction of an inert gas, for example nitrogen or helium, instead of ambient air.

Besides the aforementioned chemical stability problems associated with the use of an active-ingredient base, physical stability problems may also occur. The matrix of a formulation in which an active-ingredient base is used instead of a corresponding active-ingredient salt is often already very soft immediately after coating. Provided that the adhesiveness would rise even further after coating, it is often necessary to add additional matrix formers as early as during the preparation of the active ingredient-containing masses, so that the transdermal therapeutic system at the end of its period of application can be completely removed from the skin.

In addition, transdermal therapeutic systems having an active-ingredient base may see the occurrence of marked "cold flow", which causes the systems to adhere to the interior of their packaging or makes application and wearing of the system difficult.

The aforementioned problems with developing and producing transdermal therapeutic systems can be avoided at least in part if an active-ingredient salt is used instead of the free active-ingredient base. The use of active ingredients in the form of one of their pharmaceutically acceptable salts for transdermal therapeutic systems is advantageous in that the transdermal therapeutic systems respond more insensitively to external influences, chemical stability is better because the active-ingredient salt has fewer interactions with other ingredients or components of the system, and "cold flow" is reduced.

However, the skin permeability of pharmaceutical active ingredients in the form of a salt is substantially worse than the skin permeability of the free base of said active ingredient, and so many active-ingredient salts are not suitable for administration via the skin in a therapeutically necessary dose using a transdermal therapeutic system.

However, in order to adjust the flux rate of a transdermal therapeutic system to a certain level, i.e., to limit it, active ingredients with good skin permeability generally need a control membrane which is arranged between the skin and the active-ingredient reservoir. However, such transdermal therapeutic systems require a complicated development and production process, and so the costs for the production of the systems are high. In addition, the physical properties of the system such as flexibility and adhesiveness change as a result of the addition of the control membrane.

SUMMARY OF ADVANTAGEOUS EMBODIMENTS OF THE INVENTION

It is therefore an object of the present invention to provide a transdermal therapeutic system which utilizes the favorable permeation properties of active-ingredient bases but avoids the stability problems, wherein the flux rate thereof can be adjusted to a predetermined level without it being necessary to have a control membrane in the transdermal therapeutic system.

DETAILED DESCRIPTION OF ADVANTAGEOUS EMBODIMENTS OF THE INVENTION

The object is achieved by a transdermal therapeutic system in which the matrix or, in the case of a multilayer matrix, at least one of the matrix layers contains at least one pharmaceutical active ingredient in the form of one of its pharmaceutically acceptable salts and at least one oxide which reacts to form a base upon contact with water, and so, owing to the water coming from the skin, application of the TTS to the skin leads to an acid-base reaction between the active-ingredient salt and the hydroxide arising from the oxide, in which reaction the active ingredient in the form of its free base can be released as reaction product from the TTS, and at the same time to the formation of a poorly water-soluble layer of the hydroxide corresponding to the oxide, resulting in the active-ingredient flow being controlled.

Only when the TTS according to the invention is applied to the skin, moisture uptake into the system and, as a result, an acid-base reaction occur. For the reaction kinetics, the amount of water which the system takes up/has taken up is important. In principle, the reaction only has to be activated by water, since, in the balance of the acid-base reaction, the water which has been used is also available again after the reaction. Addition of additional water to the reaction can speed up the course of the reaction.

The present invention is based on the good permeation properties of active-ingredient bases. With the present invention, it is possible to control the flux rate for an active ingredient from a transdermal therapeutic system and to adjust it such that there is generally no need for an additional control membrane.

The flux rate can, for example, be controlled by intensifying or attenuating the acid-base reaction. If the concentration of the active-ingredient salt(s) in the preparation according to the invention is changed, this also changes the kinetics of the acid-base reaction and thus the flux rate. At a higher concentration of the active-ingredient salt, the flux rate is also increased. At a lower concentration of the active-ingredient salt(s), the flux can also be reduced.

However, in the case of oxide concentration, the system behaves differently because an additional effect needs to be considered. If the oxide concentration is increased, for example beyond the amount equimolar to the concentration of the active-ingredient salt(s), a large amount of hydroxide may be formed which is available for reaction with the active-ingredient salt(s). Consequently, the active-ingredient salt(s) is/are converted into their corresponding free bases and can be administered via the skin. However, excess, poorly water-soluble hydroxide remains in the matrix or matrix layer and forms a kind of blocking layer through which water cannot penetrate to reach further oxide in order to facilitate a further acid-base reaction. This can impede the release of active ingredient. If the concentration is reduced such that it is lower than the equimolar amount of active-ingredient salt, the acid-base reaction is likewise slowed down and the conversion of the active-ingredient salt to the base is impeded.

In embodiments with a multilayer matrix, the flux rate can also be controlled by coordination of the acid-base reaction, by dividing the active-ingredient salt(s) and/or the oxide into different matrix layers. If the active-ingredient salt(s) and the oxide are incorporated into different matrix layers, the time course of the acid-base reaction can be controlled. Here, it is also important in which order oxide-containing matrix layers and active ingredient-containing matrix layers follow each other. For example, if the oxide-containing matrix layer is situated before the active ingredient-containing matrix layer, based on the direction from which the moisture of the skin penetrates the system, the acid-base reaction is started more quickly than if the oxide-containing matrix layer only came after the active ingredient-containing matrix layer.

In embodiments with a multilayer matrix, the flux rate can also be controlled by staggering the concentrations of active-ingredient salt and/or oxide. In this way, it is possible, for example, to achieve linearity in the flux rate. If, for example, the first matrix layer has a low concentration of active-ingredient salt and oxide, and the subsequent layers have an increasing concentration of active-ingredient salt and oxide, a slow rise in the level of active ingredient and a steady release can be ensured.

The pharmaceutical active ingredient or the pharmaceutical active ingredients are present in the transdermal preparation according to the invention in the form of one or more of its/their pharmaceutically acceptable salts.

The pharmaceutically acceptable salts of pharmaceutical active ingredients are known to a person skilled in the art. Useful active-ingredient salts are particularly those whose reaction with hydroxides begins within a time frame of 0 to 24 hours after application of the preparation to the skin and whose free base exhibits good skin permeation. Particularly useful are the pharmaceutically acceptable salts of active ingredients from the group of the antidementia agents, for example memantine hydrochloride, donepezil hydrochloride, rivastigmine tartrate, the group of the antidepressants, for example bupropion hydrochloride, clomipramine hydrochloride, paroxetine hydrochloride, sertraline hydrochloride, venlafaxine hydrochloride, duloxetine hydrochloride, the group of the active ingredients for treating Parkinson's disease and/or restless legs syndrome, for example amantadine hydrochloride, pramipexol hydrochloride, ropinirole hydrochloride, selegiline hydrochloride, the group of the narcotics, for example esketamine hydrochloride, ketamine hydrochloride, the group of active ingredients for treating ADHS, for example methylphenidate hydrochloride, the group of the analgesics, for example drofenine hydrochloride, oxycodone hydrochloride, morphine hydrochloride, the group of the insulin sensitizers, for example pioglitazone hydrochloride, the group of the antihistamines, for example cetirizine hydrochloride, the group of active ingredients for treating hypertension, for example moxonidine, the group of active ingredients for treating hypotension, for example theodrenaline hydrochloride, the group of active ingredients for treating urinary incontinence and urge incontinence, for example oxybutynin hydrochloride, the group of active ingredients for preventing nausea and emesis in chemotherapies, radiation therapies and/or surgical operations, for example palonosetron hydrochloride, ondansetron hydrochloride, ramosetron hydrochloride.

Besides the hydrochloride salts, useful salts also include sulfates, phosphates, silicates, carbonates, tartrates, oxalates and similar salts of the active ingredients.

When using a combination of active ingredients in the preparation according to the invention, the ratio of active-ingredient salts to one another is freely selectable within a wide range. An appropriate ratio of active-ingredient salts is chosen by a person skilled in the art depending on the known dose-response relationship of the respective active ingredients, with regard td the desired therapeutic effect and to the required or desired dosage. The respective appropriate daily doses of known active ingredients are known to a person skilled in the art or can be found in the specialist literature.

The content of active-ingredient salt(s) in the matrix or in the active ingredient-containing matrix layers in the case of a multilayer matrix should be between 0.1 and 40% by weight, based on the dry mass of the matrix or on the dry mass of the active ingredient-containing matrix layer.

The matrix or at least one of the matrix layers of the preparation according to the invention contains at least one basic oxide which is suitable for use on skin. Useful oxides include the oxides of metals which react with water to form a base or alkaline solution. These include, for example, the alkaline earth metal oxides such as beryllium oxide, magnesium oxide and calcium oxide.

The oxide content is preferably between 0.1 and 40% by weight, based on the dry mass of the matrix or on the dry mass of the active ingredient-containing matrix layer.

In its simplest embodiment, the preparation according to the invention comprises a single-layer matrix which contains both at least one pharmaceutical active ingredient in the form of one of its pharmaceutically acceptable salts and the oxide.

In preferred embodiments, the preparation according to the invention comprises a multilayer matrix.

Particular preference is given to embodiments having a multilayer matrix in which the active ingredient and the oxide are contained in different layers of the matrix.

In this connection, the system according to the invention can be structured such that an active-ingredient flow can be set specifically by using different concentrations of active ingredient and/or oxide in the respective layers. The oxide which forms corresponding hydroxides upon contact with water acts as a control element, not only by converting the active-ingredient salt into the free active-ingredient base, but also by forming a poorly soluble layer of the corresponding hydroxide, whereby the active-ingredient flow is likewise regulated.

The matrix or at least the layer of the matrix facing the skin during use of the system comprises a pressure-sensitive adhesive polymer or a combination of pressure-sensitive adhesive polymers. "Pressure-sensitive adhesive polymers" for the purposes of the present description are understood to mean those polymers which are contained in pressure-sensitive adhesive formulations, and which are suitable for use on skin.

Preferably, the pressure-sensitive adhesive polymer is selected from the group of polymers consisting of polyacrylates, polymethacrylates, polydimethylsiloxanes, polyvinyl acetates, polyisobutylenes, styrene/isoprene/styrene block copolymers, styrene/butadiene/styrene block copolymers, polyterpenes, ethylene/vinyl acetate copolymers, rubbers and synthetic rubbers.

The proportion of the pressure-sensitive adhesive polymer/polymers is preferably from 5 to 90% by weight, based on the matrix or pressure-sensitive adhesive matrix layers.

In a preferred embodiment, the pressure-sensitive adhesive polymer or the pressure-sensitive adhesive polymers of the matrix are present in a crosslinked state. The pressure-sensitive adhesive polymers can be crosslinked by means known to a person skilled in the art, for example by using chemical crosslinkers, for example aluminum acetylacetonate or titanium acetylacetonate in the case of polyacrylates, or by means of irradiation.

Owing to the composition of the active-ingredient salt(s) and of the oxide, the preparation according to the invention may be too dry and incapable of adhering to skin under its own forces. In the case of such embodiments, the system may have an additional pressure-sensitive adhesive layer, for example also in the form of a circular adhesive strip which surrounds the active-ingredient reservoir. It is also possible to attach a pressure-sensitive adhesive covering patch.

The TTSs according to the invention have an active ingredient-impermeable, occlusive backing layer. Materials suitable for the backing layer are in particular polyesters which have a particular strength. Furthermore, it is also possible to use any other desired plastics to produce the backing layer, for example polyvinyl chloride, ethylene/vinyl acetate, vinyl acetate, polyethylene, polypropylene, cellulose derivates or combinations of the aforementioned polymers. If necessary, the backing layer can be provided with an additional layer, for example by vapor deposition with a metal or another diffusion-blocking additive such as silicon dioxide, aluminum oxide or the like.

For the removable protective layer, it is possible to use the same materials as those used for the backing layer, provided that they are removable. If necessary, the removability of a sheet can be achieved by appropriate surface treatment, for example by siliconization of the sheet. However, it is also possible to use other removable protective layers, for example polytetraethylene-treated paper, cellophane, polyvinyl chloride or the like.

The present invention also extends to processes for producing the TTSs according to the invention, which are distinguished by the fact that at least one pharmaceutical active-ingredient salt and at least one pharmaceutically acceptable basic oxide are incorporated into a preferably pressure-sensitive adhesive matrix or into at least one matrix layer. The active-ingredient salt and the oxide can be stirred into the same polymer-containing mass or into separate polymer-containing masses for the matrix. The resulting masses are processed to form sheets which, as appropriate, are laminated to one another. The resulting matrix or the resulting laminate is provided with a backing layer and a removable protective layer.

The TTSs according to the invention permit the release of active ingredient over a period of at least 24 hours, preferably at least, 72 hours, particularly preferably at least 168 hours.

At the start of treatment with the TTS according to the invention, a first TTS according to the invention is applied to the skin of the patient to be treated and, in order to continue the treatment, the applied TTS is replaced at an interval of 24, 72 or 168 hours in each case by applying a new TTS according to the invention.

Exemplary embodiments are listed below:

EXAMPLE 1

| Ingredient | % by weight |
|---|---|
| Memantine HCl | 30.0 |
| CaO | 7.5 |
| Acrylic polymer | 62.5 |

Preparation:

The appropriate amount of memantine hydrochloride is initially charged, and suspended using an organic solvent (e.g., ethyl acetate) in about ⅓ of the amount of active ingredient. After subsequent addition of the corresponding amount of an appropriate acrylate (e.g., DUROTAK® 9301), National Starch, New Jersey, stirring is carried out in order to ensure a homogeneous distribution of the active ingredient in the polymer. Calcium oxide is added to the mass with stirring and stirred further until a homogeneous suspension is obtained. The suspension is homogenized further for a maximum of 2 minutes with vigorous stirring (e.g., ULTRA-TURRAX®).

The loss by evaporation is detected gravimetrically and compensated with ethyl acetate.

After coating onto an appropriate protective sheet (e.g., polyethylene terephthalate sheet, PET), the laminate is dried and laminated with an appropriate occlusive backing layer (e.g., PET sheet). After punching out the TTSs, they are packed in an appropriate material, preferably PET.

EXAMPLE 2

The following example shows a matrix system comprising multiple layers. By applying multiple layers, it is possible to set exact active-ingredient profiles.

a) 1st Layer

| Ingredient | % by weight |
|---|---|
| Amantadine HCl | 29.9 |
| CaO | 7.5 |
| Acrylic polymer | 62.6 | b) 2nd Layer

| Ingredient | % by weight |
|---|---|
| Amantadine HCl | 30.0 |
| CaO | 4.6 |
| Acrylic polymer | 65.4 |

Preparation:

The appropriate amount of amantadine hydrochloride of the 1st layer is initially charged, and suspended using an organic solvent (e.g., ethyl acetate) in about ⅓ of the amount of active ingredient.

After subsequent addition of the corresponding amount of an appropriate acrylate (e.g., GMS 3083, Cytec Industries Inc., New Jersey), stirring is carried out in order to ensure a homogeneous distribution of the active ingredient in the polymer.

Calcium oxide is added to the mass with stirring and stirred further until a homogeneous suspension is obtained. The suspension is further homogenized for a maximum of 2 minutes with vigorous stirring (e.g., ULTRA-TURRAX®).

The loss by evaporation is detected gravimetrically and compensated with ethyl acetate.

After coating the 1st layer onto an appropriate protective sheet (e.g., PET sheet), the laminate is dried and laminated with the 2nd layer. This two-layer laminate is likewise dried and subsequently laminated with an appropriate occlusive backing layer (e.g., PET sheet). After punching out the TTSs, they are packed in an appropriate material, preferably PET.

The invention claimed is:

1. A base-form active-ingredient transdermal therapeutic system comprising an active ingredient-impermeable, occlusive backing layer, a matrix comprising either a single-layer or multiple layers, and a removable protective sheet,
   wherein at least one of the layers of the matrix contains a pharmaceutically acceptable active ingredient consisting essentially of a pharmaceutically acceptable active ingredient salt or multiple pharmaceutically acceptable active ingredient salts of said base-form active-ingredient, and at least one pharmaceutically acceptable oxide as a reactive active ingredient release agent,
   wherein said transdermal therapeutic system does not comprise a control membrane, and
   the oxide is present in a less than equimolar amount relative to said pharmaceutically acceptable active ingredient salt(s).

2. The transdermal therapeutic system as claimed in claim 1 wherein the matrix comprises at least two layers, wherein at least one of the layers of said matrix contains a pharmaceutically acceptable active ingredient salt or multiple pharmaceutically acceptable active ingredient salts, and at least one different layer of said matrix contains a pharmaceutically acceptable oxide,
   wherein the oxide is present in an amount of from 0.1 to 40% by weight, based on a dry mass for the layer(s) containing the oxide,
   said transdermal therapeutic system does not comprise a control membrane, and
   the flux rate is controlled via intensifying or attenuating said acid-base reaction, such that the concentration of said hydroxide is decreased thereby impeding the release of active ingredient.

3. The transdermal therapeutic system as claimed in claim 1, wherein the active-ingredient salt is present in an amount of from 0.1 to 40% by weight, based on a dry mass for the layer(s) containing the active-ingredient salt.

4. The transdermal therapeutic system as claimed in claim 1, wherein the pharmaceutically acceptable active-ingredient salt or multiple pharmaceutically acceptable active ingredient salts is or are selected from the group comprising hydrochloride, sulphate, phosphate, silicate, carbonate, tartrate and oxalate pharmaceutically acceptable salts of the active ingredient(s).

5. The transdermal therapeutic system as claimed in claim 1, wherein the oxide is selected from the group consisting of beryllium oxide, magnesium oxide and calcium oxide.

6. The transdermal therapeutic system as claimed in claim 1, wherein the matrix or at least one of the layers within said matrix comprises a pressure-sensitive adhesive polymer or a combination of pressure-sensitive adhesive polymers.

7. The transdermal therapeutic system as claimed in claim 6, wherein the pressure-sensitive adhesive polymer or the pressure-sensitive adhesive polymers are selected from the group consisting of polyacrylates, polymethacrylates, polydimethylsiloxanes, polyvinyl acetates, polyisobutylenes, styrene-isoprene-styrene block copolymers, styrene-butadiene-styrene block copolymers, polyterpenes, ethylene-vinyl acetate copolymers, rubbers and synthetic rubbers.

8. The transdermal therapeutic system as claimed in claim 6, wherein the pressure-sensitive adhesive polymer or the pressure-sensitive adhesive polymers are crosslinked.

9. The transdermal therapeutic system as claimed in claim 6, wherein the pressure-sensitive adhesive polymer is present in a proportion ranging from 5 to 90% by weight, based on the matrix or pressure-sensitive adhesive matrix layer.

10. The transdermal therapeutic system as claimed in claim 1, wherein said transdermal therapeutic system additionally comprises a pressure-sensitive adhesive layer.

11. The transdermal therapeutic system as claimed in claim 2, wherein oxide-containing matrix layers and active ingredient-containing matrix layers follow one another alternately.

12. The transdermal therapeutic system as claimed in claim 2, wherein the matrix comprises a layer facing skin when the transdermal therapeutic system has been applied, and said layer facing skin contains oxide.

13. The transdermal therapeutic system as claimed in claim 2, wherein the matrix layer facing the skin when the system has been applied contains active ingredient.

14. A process for producing a transdermal therapeutic system as claimed in claim 1 comprising stirring at least one pharmaceutical active ingredient in the form of at least one of its pharmaceutically acceptable salts into a polymer-containing mass, and stirring said pharmaceutically acceptable basic oxide into said polymer-containing mass or a different polymer-containing mass to form the matrix, processing the stirred polymer-containing masses to form sheets which, optionally, are laminated to one another, and providing the sheets of matrix or the laminated sheets of matrix with a backing layer and a removable protective layer.

15. A method of transdermal administration comprising applying a transdermal therapeutic system as claimed in claim 1 for transdermal release of active ingredient over a period of at least 24 hours.

16. The transdermal therapeutic system as claimed in claim 1, wherein the transdermal therapeutic system releases active ingredient over a period of at least 72 hours.

17. The transdermal therapeutic system as claimed in claim 1, wherein the transdermal therapeutic system releases active ingredient over a period of at least 168 hours.

18. The transdermal therapeutic system as claimed in claim 1, wherein the flux rate of the active ingredient of said multiple layer matrix is controlled by varying the concentration of the active ingredient salt and oxide in said matrix layers.

19. The transdermal therapeutic system as claimed in claim 1, wherein said transdermal therapeutic system consists of an active ingredient-impermeable, occlusive backing layer, a matrix, and a removable protective sheet, said matrix comprises either one or two layers, said pharmaceutically acceptable active ingredient salt or multiple pharmaceutically acceptable active ingredient salts present in each matrix layer.

20. The transdermal therapeutic system as claimed in claim 19, wherein said matrix comprises two layers, the active-ingredient salt and/or oxide concentrations are staggered and said system provides linear administration of active ingredient.

21. A base-form active-ingredient transdermal therapeutic system comprising an active ingredient-impermeable, occlusive backing layer, a matrix comprising either a single-layer or multiple layers, and a removable protective sheet, wherein each of the layers of the matrix consists essentially of pressure-sensitive adhesive polymer, a pharmaceutically acceptable active ingredient consisting essentially of a pharmaceutically acceptable active ingredient salt or multiple pharmaceutically acceptable active ingredient salts of said base-form active-ingredient, and a reactive active ingredient release agent consisting of at least one pharmaceutically acceptable oxide, wherein the flux rate is controlled via an acid-base reaction, the matrix or at least one of the layers within said matrix comprises a pressure-sensitive adhesive polymer or a combination of pressure-sensitive adhesive polymers, the pressure-sensitive adhesive polymer is present in a proportion ranging from 5 to 90% by weight, based on the matrix or pressure-sensitive adhesive matrix layer, and said matrix layer(s) is adjacent said backing layer and said protective sheet, the oxide is present in a less than equimolar amount relative to said pharmaceutically acceptable active ingredient salt(s).

22. The transdermal therapeutic system as claimed in claim 1 wherein the flux rate of said active ingredient is impeded by varying the concentration of the active ingredient and oxide.

* * * * *